(12) United States Patent
Dobbyn (10) Patent No.: US 9,587,846 B2
(45) Date of Patent: Mar. 7, 2017

(54) DUCTLESS FUME HOOD GAS MONITORING AND DETECTION SYSTEM (71) Applicant: Gregory J. Dobbyn, Raleigh, NC (US)

(72) Inventor: Gregory J. Dobbyn, Raleigh, NC (US)

(*) Notice: Subject to any disclaimer, the term of this patent is extended or adjusted under 35 U.S.C. 154(b) by 0 days.

(21) Appl. No.: 14/838,195

(22) Filed: Aug. 27, 2015

(65) Prior Publication Data

US 2015/0369501 A1 Dec. 24, 2015

Related U.S. Application Data (63) Continuation of application No. 13/765,345, filed on Feb. 12, 2013, now Pat. No. 9,121,622, which is a (Continued)

(51) Int. Cl.
*B08B 15/02* (2006.01)
*F24F 11/00* (2006.01)
(Continued)

(52) U.S. Cl.
CPC ...... *F24F 11/0001* (2013.01); *B01D 46/0036* (2013.01); *B01D 46/0086* (2013.01); *B01D 53/04* (2013.01); *B08B 15/023* (2013.01); *G01N 33/0004* (2013.01); *G01N 33/0036* (2013.01); *B01D 2253/102* (2013.01); *B01D 2253/106* (2013.01); *B01D 2257/60* (2013.01); *B01D 2257/90* (2013.01); *B01D 2257/93* (2013.01); *B01D 2258/06* (2013.01); *B01D 2259/4508* (2013.01); *F24F 2003/1621* (2013.01); *F24F 2011/0093* (2013.01); *G01N 27/66* (2013.01)

(58) Field of Classification Search
CPC .............. A62B 18/088; B01D 2273/18; B01D 46/0086; B01D 2201/52; B01D 2257/708; B01D 46/0091; B01D 35/143; B01L 1/00; B01L 2300/025; B08B 15/023; B08B 15/02; F24F 2011/0093; F24F 3/161; G01N 2015/084
See application file for complete search history.

(56) References Cited

U.S. PATENT DOCUMENTS 3,765,225 A 10/1973 Rivers
3,811,250 A 5/1974 Fowler, Jr.
(Continued)

FOREIGN PATENT DOCUMENTS

DE 19859788 C1 3/2000
EP 1806169 A1 7/2007
(Continued)

OTHER PUBLICATIONS

EP Office Action for European Patent Application No. EP 10808636.4 mailed on Dec. 7, 2015.
(Continued)

*Primary Examiner* — David A Rogers
(74) *Attorney, Agent, or Firm* — Moore & Van Allen PLLC; Jeffrey R. Gray (57) ABSTRACT A ductless fume hood suitable for the removal of various chemical materials including toxic and non-toxic gases, vapors, particles, dust and unpleasant odors from a fluid stream. The ductless fume hood uses electronic devices and software to enable real time monitoring of gas levels in parts per million.

21 Claims, 4 Drawing Sheets

Related U.S. Application Data continuation of application No. 12/541,384, filed on Aug. 14, 2009, now Pat. No. 8,372,186.

(51) Int. Cl.
*G01N 33/00* (2006.01)
*G01N 27/66* (2006.01)
*F24F 3/16* (2006.01)
*B01D 53/04* (2006.01)
*B01D 46/00* (2006.01)

(56) References Cited

U.S. PATENT DOCUMENTS

| | | |
|---|---|---|
| 4,494,403 A | 1/1985 | Bowers et al. |
| RE31,952 E | 7/1985 | Wilcox et al. |
| 4,683,762 A | 8/1987 | Aurich |
| 4,706,553 A | 11/1987 | Sharp et al. |
| 4,873,970 A * | 10/1989 | Freidank ............ A62B 18/088 128/202.22 |
| 4,946,480 A | 8/1990 | Hauville |
| 5,116,764 A | 5/1992 | Annino et al. |
| 5,240,455 A | 8/1993 | Sharp |
| 5,393,979 A | 2/1995 | Hsi |
| 5,674,381 A | 10/1997 | Den Dekker |
| 5,810,657 A * | 9/1998 | Pariseau ............ F24F 11/0076 454/61 |
| 5,856,198 A | 1/1999 | Joffe et al. |
| 6,162,281 A * | 12/2000 | Ammann ............ A62B 18/088 55/DIG. 34 |
| 6,186,140 B1 | 2/2001 | Hoague |
| 6,974,197 B1 | 12/2005 | Henry et al. |
| 6,979,363 B2 | 12/2005 | Boyd et al. |
| 7,010,960 B1 | 3/2006 | Grantham |
| 7,334,490 B2 | 2/2008 | Morse et al. |
| 7,658,787 B2 | 2/2010 | Morse et al. |
| 7,766,732 B2 | 8/2010 | Hauville |
| 2002/0072322 A1 | 6/2002 | Sharp et al. |
| 2005/0035852 A1 | 2/2005 | Paulsen |
| 2005/0040337 A1 | 2/2005 | Cox et al. |
| 2007/0105494 A1 | 5/2007 | Lin |
| 2007/0272083 A1 | 11/2007 | Hoge et al. |
| 2008/0072763 A1 | 3/2008 | Hauville |
| 2008/0156348 A1 | 7/2008 | Mimken et al. |
| 2009/0249895 A1 | 10/2009 | Mahler |
| 2009/0293580 A1 | 12/2009 | Babel et al. |
| 2009/0298192 A1 | 12/2009 | Parham et al. |

FOREIGN PATENT DOCUMENTS

| | | |
|---|---|---|
| JP | 2001062237 A | 3/2001 |
| KR | 10-2004-0066556 A | 7/2004 |
| WO | WO 2007/006757 A1 | 1/2007 |

OTHER PUBLICATIONS

Ductless Fume Cabinets, Esco Micro Pte. Ltd, available on the internet at <http:1/web.archive.org/web/20080603233301/http://www.escoglobal.com/ductless/product_1.asp>, Jun. 3, 2008.
International Search Report and Written Opinion for International Patent Application No. PCT/US2010/045036 mailed Feb. 18, 2011.
Extended Search Report for European Patent Application No. EP 10808636.4 completed on Apr. 17, 2014.
Australian Examination Report dated Sep. 8, 2014 for Patent Application No. 2010282657.
Australian Examination Report for Australian Patent Application No. 2015249130 issued on Oct. 31, 2016.

* cited by examiner

DUCTLESS FUME HOOD GAS MONITORING AND DETECTION SYSTEM

CROSS REFERENCE AND PRIORITY TO RELATED APPLICATIONS UNDER 35 U.S.C. 120

This application is a continuation of, and claims priority to both U.S. patent application Ser. No. 13/765,345 entitled "DUCTLESS FUME HOOD GAS MONITORING AND DETECTION SYSTEM," filed on Feb. 12, 2013, now U.S. Pat. No. 9,121,662 issued on Sep. 1, 2015, which is a continuation of U.S. patent application Ser. No. 12/541,384, filed on Aug. 14, 2009 and entitled "DUCTLESS FUME HOOD GAS MONITORING AND DETECTION SYSTEM", now U.S. Pat. No. 8,372,186 issued on Feb. 12, 2013, which are both hereby expressly incorporated by reference herein in their entirety.

FIELD

The present invention relates generally to ductless fume hoods including an electronic device and software to enable real time monitoring of gas levels in the exhaust plenum, interfilter monitoring port(s), and ambient laboratory air.

BACKGROUND

Ductless, or filtration, fume hoods are a specific type of fume hood that use a filtration system to remove contaminants from an air stream. Ductless hoods operate by simply forcing contaminated air from the hood enclosure through a filter to remove particulates and chemical vapors before returning the air to the laboratory environment.

Ductless hoods have several convenient advantages over laboratory installed, ducted hoods. They are mobile and portable and have minimal installation costs as they do not have to be connected to a duct system. They are environmentally friendly, as no toxic gases are released into the atmosphere. Ductless hoods also have very low operating costs, as no conditioned air is removed from the laboratory and vented outside. Instead, the exhaust air is recirculated through the filter system into the laboratory environment.

Because of the advantages listed above, ductless hoods are popular with academic laboratories and hospitals. As ductless hoods are able to be operated anywhere in the laboratory and often are made transparent on all sides and as such, they are ideal for teaching demonstrations, allowing students to surround the hood. Ductless hoods have also grown in popularity in industrial laboratories, where they can be used for specific projects with low costs.

The main drawback of ductless hoods is the potential release of toxic gases into the laboratory because of filter saturation and breakthrough. While most of the advantages of using ductless hoods are derived from the re-circulating of air from the hood back into the laboratory, this re-circulation means that the air exiting the hood must be filtered and monitored at all times. Most ductless hoods use a filter comprising activated carbon as their filtration system. Although activated carbon is highly adsorbent, the activated carbon eventually become saturated. When the activated carbon becomes saturated through the thickness of the filter, chemical vapors are no longer adsorbed and begin to break through into the exhaust.

The primary inconvenience of operating a ductless hood is the need to monitor the hood filter to ensure the safety of those working in the laboratory. If the exhaust concentration of a specific compound exceeds the allowed limits set by the United States Occupational Health and Safety Administration (OSHA) or other local limits, then the filter must be changed. Prior designs have conventionally employed a timer that sounds an alarm every given number of days, typically between six and twelve months of operation time, to notify the user that it is time to check the condition of the filter. However, studies have shown that these arbitrary alarms rarely coincide with the actual timing of filter saturation. This is not surprising, as this arbitrary method of filter monitoring does not take into account the actual use of the hood while it is running Because of the unreliability of the conventional alarms in the prior art, they are often ignored, leaving the user to test the condition of the filter whenever the user feels it might be necessary. In most cases, the user will wait until a detectable odor develops in the laboratory, which is often the point at which the concentration of the compound in the air has already exceeded the OSHA limits. In other cases where the compound being used is odorless, the user is forced to be very vigilant in checking filter efficiency, and often spends a great deal of time performing tests that are not necessary. Better methods of filter monitoring are needed to maintain the safety of the hood operator and others in the laboratory without imposing inconvenient requirements that the filter be checked more often than necessary.

Other ductless hood designs have attempted to solve this problem by installing a gas sensor downstream of the filter to detect the concentration of compounds in the filter exhaust. This effort has largely proven futile as it is not possible to monitor the hundreds of different compounds used in a laboratory with just one sensor. The sensors used in ductless hoods are typically broad range detectors without any specificity for particular compounds. Although control system read-out can be obtained for the exhaust gas concentration, it is difficult to correlate this read-out to an actual concentration of an actual gas, and report to the user if that concentration actually exceeds the OSHA exposure limits. Much of this phenomenon comes from the fact that many sensors have widely varied sensitivity to different gases. This varied sensitivity makes it very difficult to choose a level of detection for the sensor at which the alarm should be triggered, especially in a situation when multiple types of chemicals are to be used in the hood. Another major problem is that none of these alarm methods use an absolute zero reference so resulting alarm points are arbitrary. An improved ductless hood filter monitoring system would greatly improve on the safety and ease of use of ductless hoods.

Furthermore, using existing technology, it is still necessary to perform air sampling tests to confirm that the filter is actually compromised. These tests usually involve use of a gas detection tube containing a color change reagent specific to the gas to be detected. Whenever a filter alarm sounds, the user must stop work and take the time to sample the exhaust air using a hand pump before deciding if a filter change is actually necessary. More convenient methods for determining filter life are necessary to simplify compliance with safety regulations.

SUMMARY

The invention generally relates to new methods and apparatuses for monitoring gases in ductless fume hoods and chemical removal filters thus enabling real time monitoring of gas levels at various stages.

In one aspect, a ductless fume hood is described, said ductless fume hood comprising:

a hood enclosure comprising a slideable window and a baffle, wherein the slideable window is open to a room for ingress of room air into the hood enclosure for combination with contaminated air generated in the hood enclosure to form an effluent stream; optionally at least one high efficiency particulate air (HEPA) filter; at least one chemical removal filter; a detection system comprising a photo-ionization detector (PID); an exhaust stack; and a motor, wherein the motor draws the effluent stream serially through the baffle, the optional at least one HEPA filter and the at least one chemical filter for egress at the exhaust stack.

In another aspect, a method of determining the concentration of a contaminant gas in parts per million (ppm) from a sample site in a ductless fume hood is described, said method comprising:
(a) measuring the current of contaminant-free air using a PID detector and saving the measurement as a zero reading;
(b) measuring the current of a known quantity of a reference gas using the PID detector and saving the measurement as a reference gas measurement;
(c) calculating the linear regression equation based on the zero reading and the reference gas measurement;
(d) measuring the current of at least one contaminant gas from the sample site using the PID detector; and
(e) calculating the concentration of the contaminant gas from the sample site using the linear regression equation.

In still another aspect, an interfilter monitoring system is described, said system comprising:
a filter enclosure;
at least one adsorbent material located in said filter enclosure; and
at least one sampling tube located within the filter enclosure, wherein said at least one sampling tube is communicatively connected to a second valve which is communicatively connected to a detection device.

In yet another aspect, a process comprising removing at least one contaminant species from an effluent stream using a ductless fume hood is described, wherein the ductless fume hood comprises:
a hood enclosure comprising a slideable window and a baffle, wherein the slideable window is open to a room for ingress of room air into the hood enclosure for combination with contaminated air generated in the hood enclosure to form an effluent stream;
optionally at least one high efficiency particulate air (HEPA) filter;
at least one chemical removal filter;
a detection system comprising a photo-ionization detector (PID);
an exhaust stack; and
a motor, wherein the motor draws the effluent stream serially through the baffle, the optional at least one HEPA filter and the at least one chemical filter for egress at the exhaust stack.

Another aspect relates to a process of monitoring for the presence of at least one contaminant species in a gas sample withdrawn from a chemical filter, said process comprising:
positioning at least one sampling tube within a filter enclosure, wherein said filter enclosure includes at least one adsorbent material, and said at least one sampling tube or gap is communicatively connected to a detection device;
withdrawing the gas sample from within the filter enclosure and moving said sample to the detector;
measuring for the presence of the at least one contaminant species in the gas sample using the detector.

Other aspects, features and advantages will be more fully apparent from the ensuing disclosure and appended claims.

DETAILED DESCRIPTION AND PREFERRED EMBODIMENTS THEREOF

The invention generally relates to new methods and apparatuses for monitoring gases in ductless fume hoods enabling real time monitoring of gas levels at various stages. The ductless fume hood described herein is suitable for numerous uses and applications involving the handling of various chemical materials which include or produce toxic and non-toxic gases, vapors, particles, dust and unpleasant odors.

As used herein, an "Acid Sensor" corresponds to a sensor that changes pH in response to the presence of acidic gases. The change in pH is registered as a change in electrical conductivity and recorded as a change in the concentration of acid gases.

As used herein, "Set Measure" corresponds to a method for determining a change in absolute gas concentration relative to a known zero reading that is controlled by the use of a device to eliminate background ambient gases found in a normal laboratory environment. The set measure mode can provide gas concentrations in parts-per-million (ppm) for room air, exhaust air, and interfilter monitoring air.

As used herein, "Set Comparator" corresponds to a method of measuring the change in status of a filter relative to a normal condition with a new filter. A "clean air" measurement can be taken during filter change and stored in memory. Subsequent measurements are compared to the "clean air" measurement. When the difference between the "clean air" and the subsequent measurement exceeds 50% threshold limit value (TLV) for the reference chemical, filter change is imminent.

As used herein, "Interfilter Monitoring" refers to the measurement, within filter media, of gas levels within the filter.

As used herein, the "laboratory environment," the "laboratory" and "the room" are used interchangeably.

As defined herein, "substantially clean air" corresponds to air that has been scrubbed of contaminant gases using the ductless fume hood described herein, wherein at least about 95%, more preferably about 98%, even more preferably about 99%, and most preferably at least about 99.5% of the contaminant gases present upstream of the chemical filter have been removed upon passage through said filter.

As used herein, "sampling tubes" correspond to any structure having gaps or holes therein, e.g., perforations, wherein the sampling tubes can be positioned/located within a chemical filter and gas samples can be collected from the chemical filter and directed out of the filter to a detector via a connecting system. It should be appreciated by one skilled in the art that the tubes are not required to be tubular in shape, nor do they have to be straight as illustrated in the figures introduced herein. For example, the sampling tubes may be serpentine, straight, curved and/or angled. The tubes themselves may have circular, oval, square, triangular or polygonal cross-sections. The gaps or holes may be circular holes, oval holes, square holes, triangular holes, polygonal holes, slits, or any other gap that allows the gas to enter the sampling tube. Alternatively, at least one internal air gap in the filter may be constructed that allows air to freely flow from the air gap and give a representative level of the gases in this air gap at the level being assayed.

As will be appreciated by one of skill in the art, the ductless fume hood described herein may be embodied as a method, system, computer program product, or a combination of the foregoing. Accordingly, embodiments of the ductless fume hood may take the form of an entirely hardware embodiment or an embodiment combining software (including firmware, resident software, micro-code, etc.) and hardware aspects that may generally be referred to herein as a "system." Furthermore, embodiments of the ductless fume hood may take the form of a computer program product on a computer-readable medium having computer-usable program code embodied in the medium.

Any suitable computer-readable medium may be utilized. The computer-readable medium may be, for example but not limited to, an electronic, magnetic, optical, electromagnetic, infrared, or semiconductor system, apparatus, or device. More specific examples of the computer-readable medium include, but are not limited to, an electrical connection having one or more wires; a tangible storage medium such as a portable computer diskette, a hard disk, a random access memory (RAM), a read-only memory (ROM), an erasable programmable read-only memory (EPROM or Flash memory), a compact disc read-only memory (CD-ROM), or other optical or magnetic storage device. In the context of this document, a computer-readable medium may be any medium that can contain, store, communicate, or transport the program for use by or in connection with the instruction execution system, apparatus, or device.

Computer program code for carrying out operations of embodiments of the ductless fume hood described herein may be written in an object-oriented, scripted or unscripted programming language such as Java, Perl, Smalltalk, C++, or the like. However, the computer program code for carrying out operations of embodiments of the ductless fume hood described herein may also be written in conventional procedural programming languages, such as the "C" programming language or similar programming languages.

Embodiments of the ductless fume hood described herein are described below with reference to flowchart illustrations and/or block diagrams of methods, apparatus (systems), and computer program products. It will be understood that each block of the flowchart illustrations and/or block diagrams, and/or combinations of blocks in the flowchart illustrations and/or block diagrams, can be implemented by computer program instructions. These computer program instructions may be provided to a processor of a general purpose computer, special purpose computer, or other programmable data processing apparatus to produce a particular machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block(s).

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the flowchart and/or block diagram block(s). Alternatively, computer program implemented steps or acts may be combined with operator or human implemented steps or acts in order to carry out an embodiment of the ductless fume hood described herein.

In one aspect, the ductless fume hood apparatus described herein relates to an improved system using electronic devices and software that enable real time monitoring of gas levels in parts per million. Preferably, the detector used to enable ppm measurements is a PID detector. In another aspect, the ductless fume hood apparatus described herein contains an improved system for monitoring filter life, wherein the efficiency of the filter can be easily and reliably monitored. Although containment of chemical vapors is referred to throughout the application, it should be appreciated that an embodiment could also be used for the containment of biological vapors using the appropriate filters and sensors.

Referring to the drawings, throughout this description, like elements are referred to by like numbers as shown in the drawings.

Figure 1:
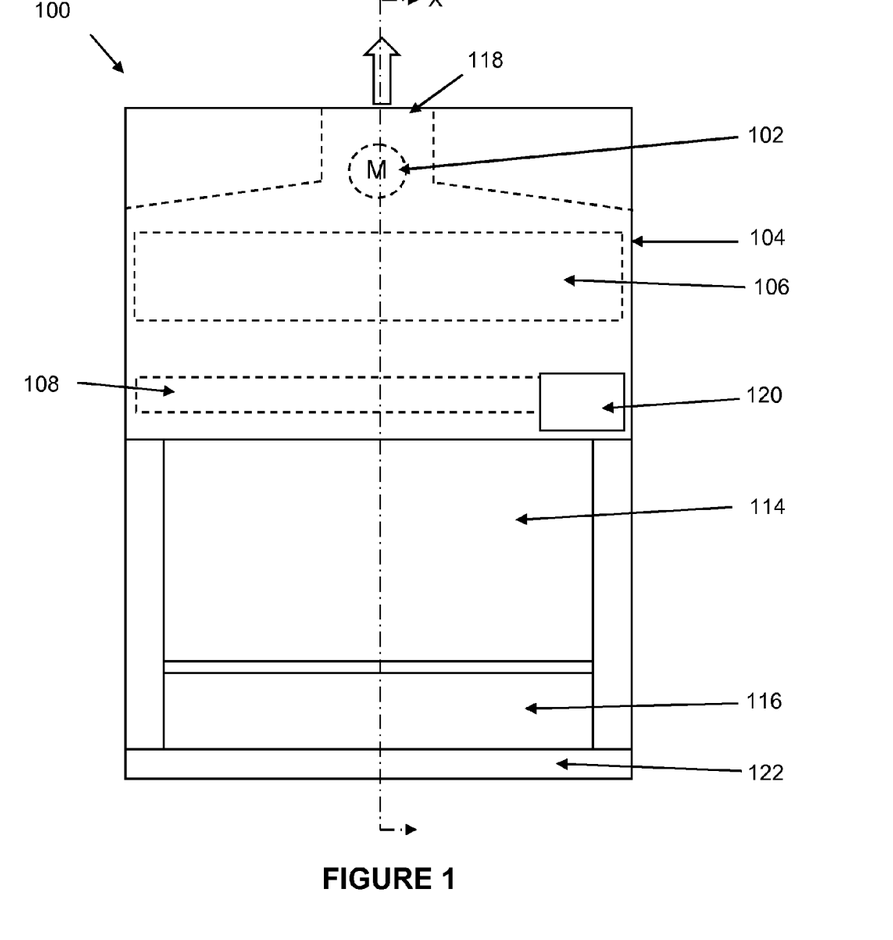
FIG. 1 illustrates a front view of a ductless fume hood described herein.

One embodiment of the apparatus of the present invention is a ductless fume hood 100 as shown in FIG. 1. The ductless fume hood 100 comprises a hood enclosure bounded on three sides and on the front by a slideable sash window 114, preferably made of tempered glass. The sides of the hood enclosure may be made of glass when transparency is preferred, otherwise the sides are made of a chemically resistant material. The sliding sash window 114 adjusts to various heights by sliding behind into the front panel 104 to allow the hood operator access to the hood enclosure. The bottom surface 122 of the hood enclosure is a work surface made of polypropylene, stainless steel, Trespa or soapstone, preferably Trespa, which allows for easy maintenance and clean up of spills. A motor 102 is used to pull air from the laboratory environment through the opening 116 in the sliding sash window 114, where it will combine with chemical vapors present in the hood to form an effluent stream. With the assistance of the motor, the effluent stream passes through the filter(s) 106 (and optionally 108 and/or 110). Filtered air is then pulled into the motor compartment, through the motor 102, and pushed out the top of the hood through the exhaust stack 118 back into the laboratory environment. The entire operation may be controlled and/or programmed by users at control pad 120, which can optionally be positioned at a location that is ADA compliant.

It should be appreciated by one skilled in the art that the fume hood may include any number of electrical outlets, electrical switches, sink(s), faucet(s), burning gas fixture(s), and lighting, and that the fume hood may be positioned on a base cabinet to achieve an optimum working height. Further, the sliding sash window 114 may be raised or lowered between a present high and low point manually or using an electric switch or the operating system.

Figure 2:
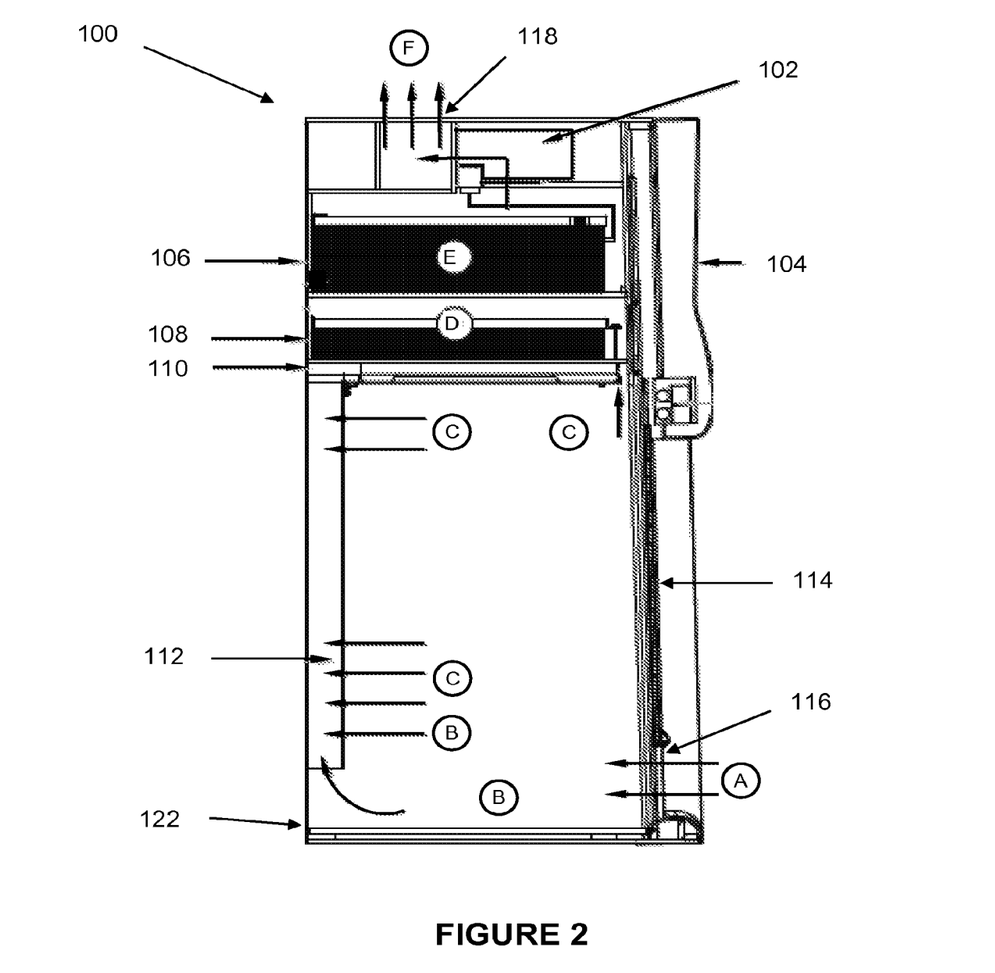
FIG. 2 illustrates a cross section of the ductless fume hood of FIG. 1 taken along line X.

A side cross sectional view of FIG. 1 taken along line X is shown in FIG. 2. The motor 102 creates an air stream up from the sash window opening 116 through the baffle 112, through an optional pre-filter 110 for the removal of large particulates, e.g., greater in size than about 0.5 microns, through an optional high efficiency particulate air (HEPA) filter 108 for the removal of particulates generally smaller in size than about 0.5 microns, through at least one chemical removal filter 106 for the removal of gases, and through the motor 102 for exhausting into the laboratory through the exhaust port 118. The electronics of the system are contained in the electronics panel which can be positioned behind the front panel 104 and can be controlled by the microprocessor control panel 120. The filters 106, 108, 110 can be accessed via the front panel 104 for easy replacement. Particulate removal filters such as 108 and 110 are particularly useful in pharmaceutical laboratories, clean rooms, etc.

In practice, laboratory air enters the fume hood at A, and is mixed with contaminated fume hood air B, the mixture of which is pulled into the baffle 112 at C. The contaminated air (or "effluent stream") is scrubbed free of particulates at D and chemicals at E before being exhausted back into the laboratory at F.

It should be appreciated by those skilled in the art that a preferred embodiment includes the placement of the motor 102 downstream between the filters and exhaust stack whereby the motor draws the room and contaminated air through the filters, however, the motor may be positioned such that the room and contaminated air are pushed through the filters as well. In another alternative, when the HEPA filter 108 is present, the motor is placed between the HEPA filter 108 and the chemical filter(s) 106. Preferably the motor is capable of moving air in a range that provides a face velocity of between 60 linear feet per minute (LFM) to 120 LFM in a smooth, laminar manner. The motor may be operated manually or automatically through the operating system.

Figure 4A:
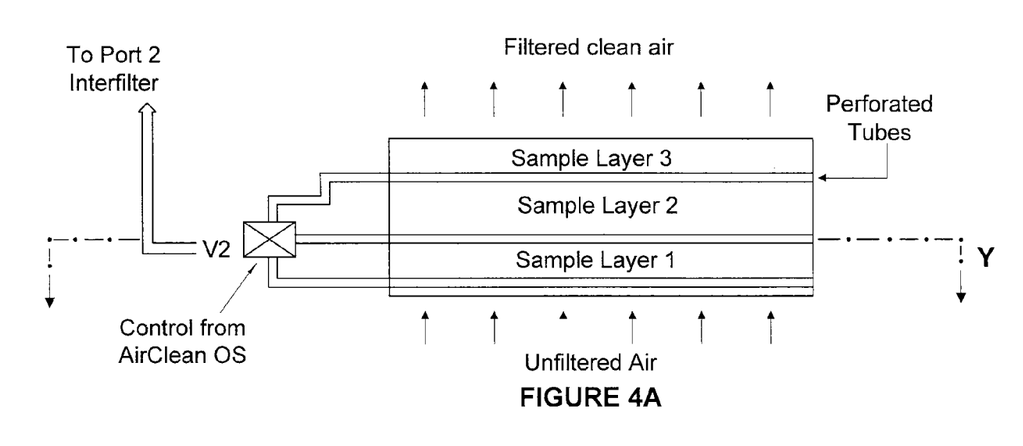
FIG. 4A illustrates a cross section of the interfilter monitoring system of the ductless fume hood described herein.

The chemical filter(s) used in the ductless fume hood described herein preferably include activated carbon. In general, standard activated carbon filters work at an efficiency of typically higher than 95% across a broad spectrum of chemical compounds. In order to increase adsorptive efficiency for specific applications, specialty carbon filters impregnated with other compounds may also be used. A non-limiting example of a specialty carbon filter is a filter in which the carbon media is impregnated with an oxidizing agent to oxidize formaldehyde and glutaraldehyde fumes. This type of filter is useful for specialty applications such as hospital pathology and endoscopy, which involve these compounds. Another example of a specialty carbon filter is a filter in which silica, alumina, potassium permanganate or combinations thereof are incorporated into the filter with the activated carbon. For example, in a preferred embodiment, the chemical filter(s) include activated carbon and silica. Filters including combined media may be arranged in differing layers, for example, silica, activated carbon, silica, etc. or activated carbon, silica, activated carbon, etc. Alternatively, the silica and activated carbon filter can be a homogeneous mixture of the two media. In a preferred embodiment, the chemical filter(s) are arranged as layers, for example as illustrated in FIG. 4A. Preferably the filter structure comprises a bonded matrix so that the filter is substantially devoid of dust.

It is readily understood by those skilled in the art that environmental factors may also affect the adsorptive efficiency of the hood. The ambient temperature of the laboratory and the contaminated air must be kept to a minimum, as higher temperatures lead to lower efficiency of adsorption. Relative humidity must also be kept to a minimum as high relative humidity can cause the chemical filter(s) to adsorb water molecules in the place of chemical vapors.

The construction of the chemical filter(s) also affects the adsorption efficiency of the hood. A filter with a thicker media bed will have a longer contact time during which a larger amount of chemical vapor will be deposited in the filter bed by adsorption. In order to maximize this contact time, the air volume passing through the hood and the filter is preferably low, however, it is necessary that the inflow velocity of the hood (through the opening 116 in the sliding sash window 114) be maintained at a high enough rate to ensure proper containment of vapors in the hood while still maintaining the residence time of the air in the filtration bed for maximum adsorption to occur.

It should be appreciated that the ductless fume hoods of the invention may include one or more chemical filters, for example, two, three, four, five, etc., that may be arranged serially or in parallel. The chemical filters can be manufactured to be mateably accommodated in the ductless fume hood. When the chemical filters need replacing, for example, the filter efficiency drops below a specific value or a different filtering media is required for removal of a chemical, the filters can be easily removed and replaced with a new filter.

Figure 3:
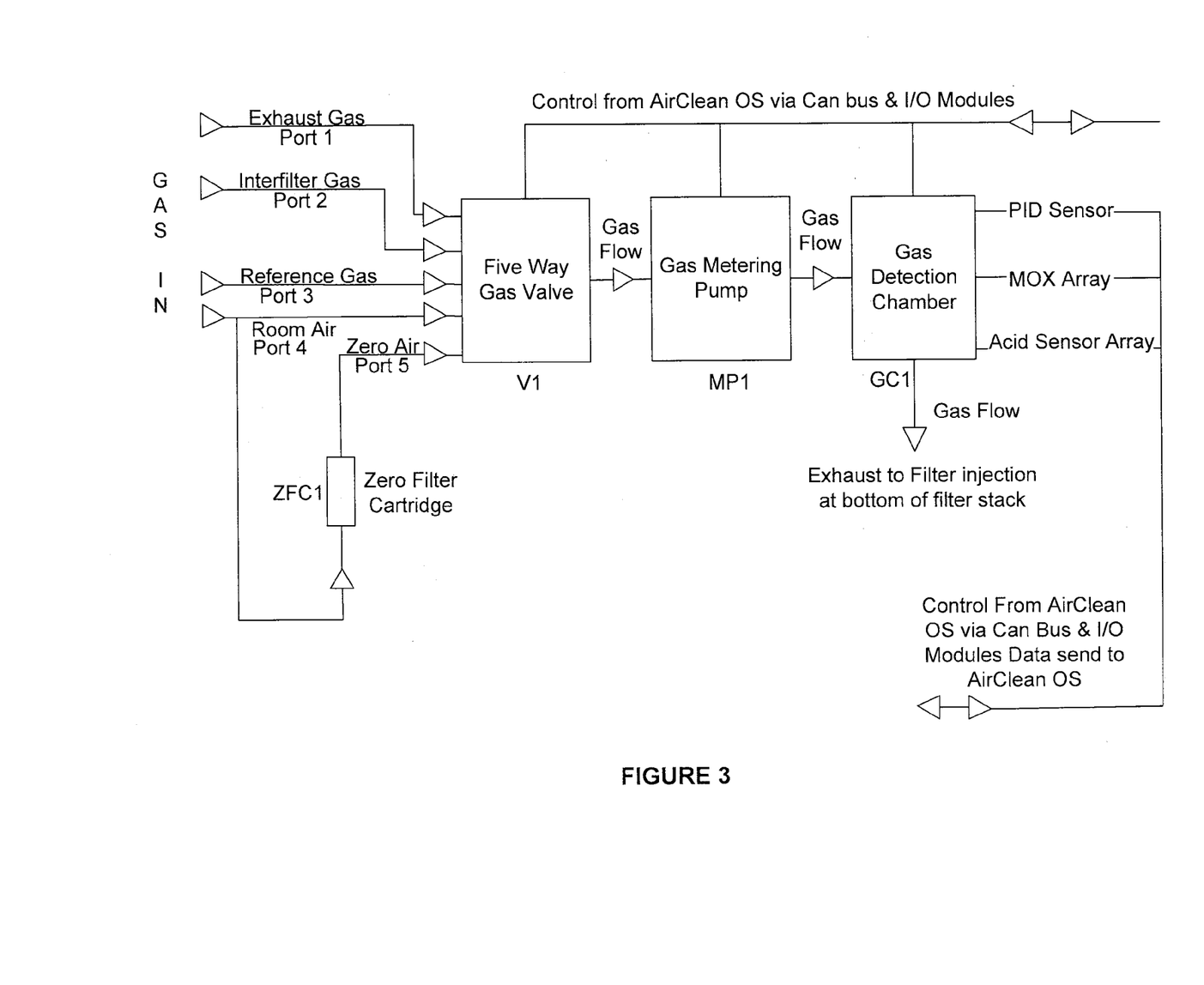
FIG. 3 is a flow diagram of the detection system of the ductless fume hood described herein.

All current ductless fume hoods use a comparator system to measure in real time the efficacy of the filtration bed, however, a quantifiable reading in absolute ppm by a real time monitoring system is not presently available. Advantageously, not only can readings in ppm be obtained using the system and process described herein, but as illustrated in FIG. 3, air can be sampled from multiple locations including, but not limited, exhaust gas from the exhaust plenum, the interfilter monitoring port, and the laboratory environment. The system is controlled by an operating system that provides monitoring and control of microprocessors and input and output devices that are connected using a controller-area network (CAN or CAN bus). The operating system will prompt the opening of the selector valve V1 of the air that is to be monitored and determine how long to pump the air, using the metering pump MP1, to the gas detection chamber GC1 based on the gas flow and volume of the gas detection chamber GC1. The operating system will also select the detector for chemical qualitation or quantitation based on gas to be monitored and following qualitation/quantitation, the operating system will evacuate the air to the entry of the filter 106 in the ductless fume hood. Detectors include, but are not limited to, a PID detector, a Metal Oxide sensor array (MOX sensor), an acid array sensor, or any combination of the three. For example, when in set measure mode, the PID detector is used and the concentration of gases in absolute ppm can be provided. When in set comparator mode, any of the PID, MOX or acid array sensors may be used.

Photoionization detectors (PIDs) are conventionally used to detect the presence of chemical compounds in air. When a molecule is exposed to high-energy photons of the appropriate photon energy, the molecule will become ionized. A pair of electrodes are arranged to be exposed to the ionized molecule such that the electrodes are electrically insulated from each other and are maintained at a voltage differential from each other. The ion is repelled from the higher voltage electrode and attracted to the lower voltage electrode. When a fluid stream is exposed to the high-energy photons, and a number of ions are produced, a measurable current is generated.

Conventionally, a PID that is used in an instrument for the purpose of detecting chemical compounds in air includes: an ultraviolet (UV) radiation source as a source for high energy photons and associated electronic circuitry for driving the UV radiation source; an ionization cell into which the output of the UV radiation source is directed, a means for a sample of gas to enter and exit the ionization cell; and two or more electrodes electrically insulated from each other and held at a voltage differential and associated electronic circuitry to maintain the voltage differential, the electrodes having a size, shape, and orientation to effectively produce a current when exposed to ions. A PID alone typically cannot provide a user with information to distinguish the specific molecules and concentrations of a number of types of molecules that are in a sample. The UV source will emit photons of a specific energy and any molecules that have an ionization energy lower than the energy of the photons will become ionized. If there is a single type of molecule present in the sample that has an ionization energy lower than the energy of the photon, a current will be generated and if compared against a known reference of the same type of molecule, a concentration of the molecule in the sample can be determined. However, if there is more than one type of molecule that is thus ionized, the user will be unable to discern the molecules that are present, the concentrations that are present, or the number of different types of molecules present. The selection of a PID sensor for the ductless fume hood described herein is readily determinable by one skilled in the art.

Metal oxide (MOX) sensors are well known in the art. A MOX device detects the presence of gas in ambient air. The device typically includes a sensor provided on a heated substrate which includes two metallic electrodes connected to the sensor. The presence of gas posing a hazard is detected by a sensible change in the resistance of the sensor by means of the electrodes that are incorporated in a suitable electric circuit. The selection of a MOX sensor for the ductless fume hood described herein is readily determinable by one skilled in the art.

In set measure mode, the gas to be measured can be determined in real time in parts per million. An example of the process includes taking an absolute zero reading prior to taking a measurement of the exhaust air, ambient (laboratory) air or interfilter air. The operating system may be programmed for automatic monitoring or the user may manually request instant monitoring. Referring to FIG. 3, to take a zero reading (also referred to as "contaminant-free air") the operating system instructs valve V1 to open thereby directing air through the zero filter cartridge ZFC1 by the metering pump MP1 into the gas detection chamber GC1 and the measurement is taken by the PID and saved as absolute zero. Zero filter cartridge ZFC1 comprises gas phase filtration media that removes all background contamination in the room air as discussed further below. Once absolute zero has been established the operating system instructs valve V1 to allow a reference gas (see, e.g., port 3) to be pumped by the metering pump MP1 into gas detection chamber GC1 for measurement with the PID. The reference gas has a known concentration in ppm and is chosen relative to the application to be used in the ductless fume hood. Examples of reference gases include, but are not limited to, isobutylene and other known low TLV chemicals. Once the operating system has the zero air and the known reference gas measurement, a line equation generated to enable unknown concentrations to be calculated, as readily understood by one skilled in the art. The operating system now introduces air containing unknown concentrations of gases from the interfilter monitoring port, the room air port or the exhaust gas monitoring port to gas detection chamber GC1 (via valve V1 using metering pump MP1), the gases are detected using the PID detector and the concentration of the gases can be calculated by the operating system in ppm and displayed on the control panel 120. Alternatively, or in addition, the operating system directs gas concentrations to alarm circuits and/or to external computers via TCP/IP and/or Ethernet connections.

The zero filter cartridge can be made of high nuclear grade carbon that removes trace contaminants of most chemicals found in the laboratory. The filter is preferably changed whenever the main chemical filter(s) are changed. Since the operating system described herein allows the user to detect levels of contaminants in the laboratory air, high contaminant levels, e.g., above 5 ppm, would also indicate to the user that the zero filter cartridge should be changed more often. In one embodiment, the operating system can be manually or automatically programmed to store the detector reading of a new zero filter cartridge, which may be stored as a "zero" ZFC value, and all subsequent readings compared thereto. When it is clear that the subsequent readings can no longer be zeroed or are statistically different than the zero ZFC value, an alarm will sound and the system will shut down.

It should be appreciated by one skilled in the art that the arrangement illustrated in FIG. 3 is non-limiting. In other words, although valve V1 is illustrated as a five-way valve, other arrangements are contemplated including, but not limited to, five individual valves all connected to the metering pump MP1 wherein each of exhaust gas, interfilter gas, reference gas, room air and contaminant-free air have their own valve. Alternatively, valve V1 may be a two-way, three-way or four-way valve whereby additional valving is upstream of valve V1. For example, valve V2 can be directly attached to the metering pump MP1 and as such, valve V1 no longer is required to be a five-way valve.

In set comparator mode, the efficiency or "status" of the filter(s) can be determined in real time. The operating system may be programmed for automatic monitoring or the user may request instant monitoring. A "clean air" measurement can be taken during filter change from the interfilter monitoring port and stored in memory. Subsequent measurements of the interfilter monitoring port are compared to the "clean air" measurement. When the difference between the "clean air" and the later measurement exceeds 50% threshold limit value (TLV) for the reference chemical, filter change is imminent. Set comparator gas detection methods can be determined using the PID sensor, the MOX sensor and the acid sensor.

Disadvantageously, prior art filtration systems have been designed to only detect the presence of contaminants before and/or after passage through a chemical filter and as such, it is impossible to understand the status of the chemical filter, e.g., the extent of filter saturation. To overcome this deficiency, another aspect of the ductless fume hood described herein is the use of interfilter monitoring which allows for monitoring of filter conditions at different layers in the filter. For example, referring to FIG. 4A, a series of sampling tubes are positioned in the direction of gas flow in series within the chemical filter(s) and are connected to valve V2. Valve V2

Figure 4B:
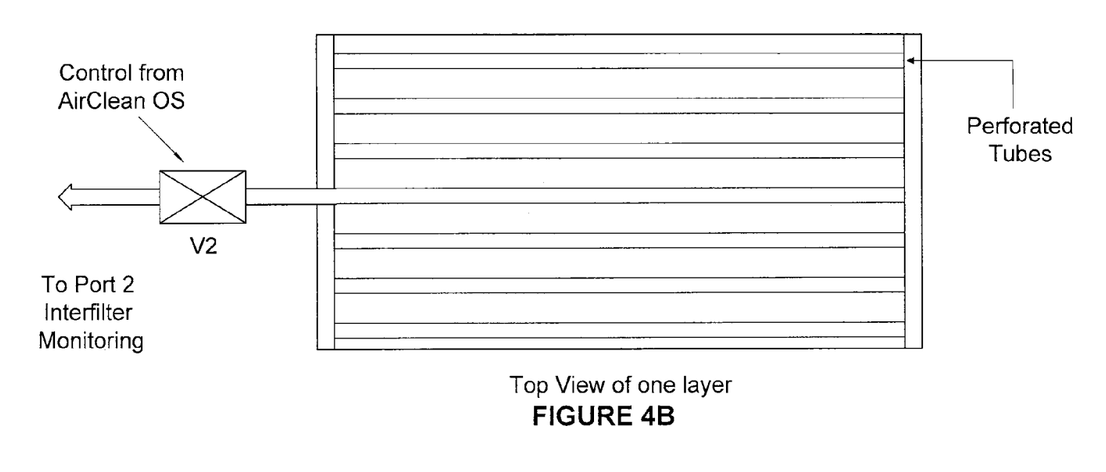
FIG. 4B illustrates a cross section of the interfilter monitoring system of FIG. 4A taken along line Y.

(FIG. 4A) is communicatively connected to valve V1 in FIG. 3. It should be appreciated by one skilled in the art that although three sampling tubes are illustrated in FIG. 4A, the interfilter monitoring system is not limited as such. Accordingly, the interfilter monitoring system may include one, two, three, four, or five or more sampling tubes positioned therein in series, preferably three. As illustrated in FIG. 4B, the sampling tubes are not only positioned in the direction of gas flow in series, but also along the plane in sample layers 1, 2, and 3. For example, FIG. 4B is the view of the filter illustrated in FIG. 4A along line Y in sample layer 2, whereby the number of sampling tubes in the plane are seven, although it should be appreciated than more or less tubes may be positioned in the Y plane.

The process of using the interfilter monitoring system includes the operating system directing valve V2 to open at sample layer 1 and sending the air sample to gas detector GC1 via valve V1 using gas metering pump MP1 (see, FIG. 3). The measurement of the air sample can be made in either set measure and/or set comparator mode. The measurement of sample layer 1 is recorded. The operating system then switches to open valve V2 and directs the system to measure the air from sample layer 2 and record it. The operating system then switches to open valve V2 and directs the system to measure the air from sample layer 3 and record it. The operating system tracks the time Ti when sample layer 1 reaches the TLV for the chemical being monitored by the operating system. Once the TLV has been reached at sample layer 1, a timer is started and begins to record T2. When the operating system registers that sample layer 2 has also reached the TLV for the chemical being monitored (T2), a calculation is made by the operating system as to the estimated time required for sample layer 3 to also reach the TLV. The estimated remaining life of the filter (ESTF) is then displayed in days of use remaining on the control panel 120 and alternatively sent to external computers via TCP/IP and/or Ethernet connections. Once the level of the gas being monitored at sample layer 3 exceeds the TLV, the operating system switches all monitoring to the exhaust plenum (see, Port 1 in FIG. 3) and alerts the user when the level of gas in the exhaust exceeds 50% TLV. At 100% TLV an alarm is generated that either switches the system to bypass mode or begins a normal shutdown sequence. Monitoring the exhaust gases is useful because the chemical filter(s) can start to desorb gases when close to maximum capacity.

Another aspect of the ductless fume hood described herein relates to the operating system in general, wherein the operating system is pre-programmed with an onboard chemical database including chemicals approved for use in the ductless fume hood with the existing filter technology. The operating system may be connected to external computers via TCP/IP and/or Ethernet connections for automatic or manual uploading of additional chemicals as more are approved for use in the ductless fume hood with the existing filter technology. In practice, the user may select one of the chemicals from the database and the operating system confirms that the chemical filter(s) is capable of removing said chemicals from the contaminated air. Further, the operating system will select the detector that is compatible with said chemical. For example, if the chemical will damage the PID, the operating system will not enter set measure mode. When more than one chemical is selected, the chemical database, which includes the TLV values for each chemical, identifies the selected chemical with the lowest TLV and that chemical will be used as the zero reading in set measure (assuming the chemical can be detected using a PID) and/or the reference chemical in set comparator mode. In the event that the chemical filter(s) are not compatible with the selected chemical, the system will sound an alarm and the ductless fume hood will not go on. The user will not be able to override the operating system with respect to the chemical(s) to be monitored and the appropriate chemical filter(s) and compatible detectors.

The control panel 120 is preferably a touch screen which allows the user to program, monitor and/or control the ductless fume hood. For example, the control panel may allow the user to monitor and control the motor blower speed, lights, purging, shutdown, users, gas detection, energy use, hood temperature, setup, electrical outlets, burning gases, timers, filters, system data, communication with external computers, etc. It should be appreciated that the control panel 120 has been described as being attached to the ductless fume hood as a touch screen, however, other alternatives include the use of keyboards and other computing devices and screens that are communicatively connected to the ductless fume hood, as readily understood by one skilled in the art.

The operating system is preferably pre-programmed with an alarm set point for specific applications. Once a reliable set point is established, the user will not be required to perform manual air sampling and will be able to rely on the alarm system to determine when the filter is no longer effective. That said, preferably, the ductless fume hood of the invention does include manual sampling ports so that users may use colorimetric gas sampling tubes to analyze for the presence of contaminants. This program allows for the added convenience of being able to rely on an alarm without compromising the user's safety.

Another aspect of the ductless fume hood described herein relates to the use of radio frequency identification (RFID) technology to ensure that the operating system, which includes a pre-programmed chemical database, accurately identifies whether the chemical filter(s) will efficaciously remove a pre-selected chemical species from the effluent stream. In one embodiment, the chemical filter(s) (e.g., 106 in FIG. 1) include at least one RFID tag located on or in the construction of the chemical filter(s), wherein said RFID tag is readable by an RFID detector when the chemical filter is inserted into the ductless fume hood. Specifically, the RFID detector is positioned within the ductless fume hood so that the RFID tag is proximally located relative to the RFID detector upon insertion of the chemical filter(s) in the ductless fume hood. In another embodiment, the chemical filter(s) includes an RFID tag that can be detachably removed from the chemical filter(s) prior to insertion of the filter(s) into the ductless fume hood, wherein the detachable tag is swiped by an externally located RFID detector on the ductless fume hood. For example, the tag may be an RFID card having the dimensions of a credit card, a keyfob or any other object that can include the RFID tag and can be detachable from the new chemical filter(s). Regardless of the detection setup, the RFID detector sends all information relating to the chemical filter(s) to the operating system so that the operating system can ensure that the ductless fume hood is operating safely and efficaciously.

Once the operating system has read the RFID tag it will check the chemical database automatically to ensure that the chemicals selected in the current application may be used with the filter now to be installed. An alarm would be generated if there is no match between the filter and the chemicals to be used.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art, based on the disclosure herein. The invention therefore is to be broadly construed, as encompassing all such variations, modifications and alternative embodiments within the spirit and scope of the claims hereafter set forth.

What is claimed is:

1. A ductless fume hood comprising:
   a hood enclosure comprising an inlet and an exhaust stack, wherein the hood enclosure is open to a room for ingress of room air into the hood enclosure through the inlet for combination with contaminated air generated in the hood enclosure to form an effluent stream;
   a detection system comprising a photo-ionization detector (PID) configured for detecting a chemical compound in the effluent stream;
   wherein the hood enclosure is configured to include at least one chemical removal filter;
   wherein the PID is configured to operate in either a set measure mode or in a set comparator mode, wherein the set measure mode is configured to determine a change in absolute gas concentration relative to a known zero, and wherein the set comparator mode is configured to measure the change in status of the at least one chemical filter related to a normal condition with a new filter; and
   wherein the effluent stream is drawn into the hood enclosure through the opening; and through the at least one chemical removal filter for egress at the exhaust stack.

2. The ductless fume hood of claim 1, wherein when operating in the set comparator mode the normal condition with the new filter is compared to later measurements, and a notification of a filter change is made when one of the later measurements exceeds a threshold limit value (TLV) of the normal condition.

3. The ductless fume hood of claim 1, wherein when operating in the set measure mode the detection system is configured to:
   take a zero reading of the room air using the PID;
   take a known reading of a reference gas using the PID;
   take an unknown reading of the room air, interfilter air, or exhaust air using the PID; and
   calculate a concentration of the chemical compound in the unknown reading of the room air, the interfilter air, or the exhaust air.

4. The ductless fume hood of claim 3, wherein the room air used for the zero reading is directed through a filter cartridge to remove background contamination in the room air.

5. The ductless fume hood of claim 3, wherein the detection system is configured to take the unknown readings of the room air, the interfilter air, and the exhaust air using the PID, and calculate the concentration of the chemical compound in the unknown reading of the room air, the interfilter air, and the exhaust air.

6. The ductless fume hood of claim 3, wherein the detection system further comprises at least a first gas valve that switches between the room air, the interfilter air, the exhaust air, and the reference gas.

7. The ductless fume hood of claim 6, wherein the detection system further comprises a gas metering pump and a gas detection chamber operatively coupled to the first gas valve.

8. The ductless fume hood of claim 1, wherein the detection system further comprises:
   a metal oxide (MOX) detector configured to detect the chemical compound in the effluent stream in the set comparator mode; or
   an acid array sensor configured to detect the chemical compound in the effluent stream in the set comparator mode.

9. The ductless fume hood of claim 1, further comprising:
   the at least one chemical removal filter; and
   at least one high efficiency particulate air (HEPA) filter.

10. The ductless fume hood of claim 9, wherein the detection system further comprises at least one sampling tube, and wherein the at least one sampling tube passes through the at least one chemical removal filter.

11. A detection system for a ductless fume hood, comprising:
    a photo-ionization detector (PID) configured to detect a chemical compound in an effluent stream within the ductless fume hood;
    a metal oxide (MOX) detector or an acid array sensor configured to detect the chemical compound in the effluent stream;
    wherein the detection system operates in either a set measure mode or in a set comparator mode;
    wherein when operating in the set measure mode the PID is used and is configured to determine a change in absolute gas concentration relative to a known zero; and
    wherein when operating in the set comparator mode the PID, or the metal oxide or the acid array sensor, is used and is configured to measure the change in status of at least one chemical filter related to a normal condition with a new filter.

12. The detection system for the ductless fume hood of claim 11, wherein when operating in the set comparator mode the normal condition with the new filter is compared to later measurements, and a notification of a filter change is made when one of the later measurements exceeds a threshold limit value (TLV) of the normal condition.

13. The detection system for the ductless fume hood of claim 11, wherein when operating in the set measure mode the detection system is configured to:
    take a zero reading of the room air using the PID;
    take a known reading of a reference gas using the PID;
    take an unknown reading of the room air, interfilter air, or exhaust air using the PID; and
    calculate a concentration of the chemical compound in the unknown reading of the room air, the interfilter air, or the exhaust air.

14. The detection system for the ductless fume hood of claim 13, wherein the room air used for the zero reading is directed through a filter cartridge to remove background contamination in the room air.

15. The detection system for the ductless fume hood of claim 13, wherein the detection system further comprises at least a first gas valve that switches between the room air, the interfilter air, the exhaust air, and the reference gas.

16. The detection system for the ductless fume hood of claim 15, wherein the detection system further comprises a gas metering pump and a gas detection chamber operatively coupled to the at least first gas valve.

17. The detection system for the ductless fume hood of claim 11, further comprising the at least one chemical filter, wherein the at least one chemical filter comprises:
    a filter enclosure;
    at least one absorbent material located in the filter enclosure;

at least one sampling tube passing through the filter enclosure and the at least one absorbent material, wherein the interfilter air is captured from the at least one sampling tube.

18. The detection system for the ductless fume hood of claim 17, wherein the at least one chemical filter comprises at least two sampling tubes positioned in series in the direction of flow of the effluent stream.

19. A method for using a detection system within a ductless fume hood, the method comprising:
  drawing room air into a hood enclosure through an inlet, wherein the room air combines with contaminated air within the hood enclosure to form an effluent stream;
  drawing the effluent steam through at least one chemical filter for egress at an exhaust stack;
  operating the ductless fume hood in either a set measure mode or in a set comparator mode;
  wherein when operating in the set measure mode a photo-ionization detector (PID) is used and is configured to determine a change in absolute gas concentration relative to a known zero; and
  wherein when operating in the set comparator mode the PID, or a metal oxide or an acid array sensor, is used and is configured to measure the change in status of the at least one chemical filter related to a normal condition with a new filter.

20. The method for using the detection system within the ductless fume hood of claim 19, wherein operating in the set measure mode comprises:
  taking a zero reading of the room air using the PID;
  taking a known reading of a reference gas using the PID;
  taking an unknown reading of the room air, interfilter air, or exhaust air using the PID; and
  calculating a concentration of the chemical compound in the unknown reading of the room air, the interfilter air, or the exhaust air.

21. The method for using the detection system within the ductless fume hood of claim 19, wherein operating in the set comparator mode comprises:
  comparing the normal condition with the new filter to later measurements; and
  providing a notification of a filter change when one of the later measurements exceeds a threshold limit value (TLV) of the normal condition.

* * * * *